United States Patent [19]

Shoesmith

[11] Plant 5,062

[45] Jun. 21, 1983

[54] CHRYSANTHEMUM NAMED BURGUNDY

[75] Inventor: Leonard H. Shoesmith, Westfield-Woking, England

[73] Assignee: Pan-American Plant Company, Parrish, Fla.

[21] Appl. No.: 313,934

[22] Filed: Oct. 22, 1981

[51] Int. Cl.[3] ..... A01H 5/00

[52] U.S. Cl. ..... Plt./76

[58] Field of Search ..... Plt./76

*Primary Examiner*—Robert E. Bagwill

*Attorney, Agent, or Firm*—Chas. W. Rummler

[57] ABSTRACT

A new and distinct dark pink decorative chrysanthemum intended for five inch or six inch pots and having an almost completely double composite inflorescence with slightly quilled florets that reveal a pale pink under side, the blooms being of medium size and profusely produced to provide a mound of color above an abundant display of foliage. This plant may be ground the year around with a nine-week response, having its best performance from April through December.

4 Drawing Figures

BACKGROUND OF THE NEW PLANT

This new chrysanthemum cultivar originated as a seedling of unknown parentage which was discovered by me in 1976 growing in a field of chrysanthemum plants maintained at West Chicago, Ill., for breeding purposes and in the hopes of finding new and unusual varieties having commercial merit. This plant attracted particular notice because of the distinctive coloration of its blooms, which have dark pink florets slightly quilled to reveal the light pink color of the under side. Accordingly, this new plant was propagated under my direction by means of vegetative cuttings and was subsequently propagated through a series of generations to test its adaptability for commercial production. Several successive generations of this new plant have shown that its novel characteristics hold true from generation to generation and appear to be firmly fixed and, accordingly, this new plant is now being propagated for commercial purposes at West Chicago, Ill., and at Cortez and Parrish, Fla.

DESCRIPTION OF THE DRAWINGS

This new chrysanthemum plant is illustrated by the accompanying drawings, of which sheet one is a full-color photographic rendition of a potted plant in full bloom to illustrate its plant and flower formations; sheet two is a photographic close-up face view of flowers of this new plant which has been hand painted to show the true colors of the blooms according to specification; sheet three is a machine copy of a photoprint showing the front side of typical leaves of this new variety; and sheet four is a similar print showing the reverse side of the leaves shown in sheet three.

DESCRIPTION OF THE NEW PLANT

The following is a detailed description of my new chrysanthemum plant based upon observations of plants grown at West Chicago, Ill., and made during the winter of 1980–1981, the color renditions being according to The R.H.S. Colour Chart published by The Royal Horticultural Society of London, England.

THE PLANT

Origin: Seedling.

Parentage: Unknown.

Classification:

*Botanic.*—*Chrysanthemum morifolium.*

*Commercial.*—Pot chrysanthemum.

Form: Perennial herbaceous bush of upright shape.

Height: Varies according to growing conditions.

Branching character: Caespitose under normal conditions.

Growth: Vigorous, strong and upright.

Growth rate: Typical chrysanthemum.

Foliage:

*Quantity.*—Abundant.

*Size of leaf.*—Up to about 90 mm. long and about 60 mm. wide.

*Shape of leaf.*—Lanceolate with cleft margins.

*Texture.*—Leathery.

*Ribs and veins.*—Pinnate.

*Color.*—Upper side — 147A. Under side — 147B.

*Petioles.*—Up to about 25 mm. long.

THE BUD

Form: Globular.

Size: The size varies in both diameter and depth.

Opening rate: Typical chrysanthemum.

Color of florets:

*When phyllaries first divide.*—72A.

*When florets begin to unfurl.*—72A.

Phyllaries:

*Number.*—Approximately 17.

*Shape.*—Lanceolate.

*Color.*—147C.

Peduncle:

*Character.*—Rigid and erect.

*Length.*—Up to about 17 cm.

*Surface aspect.*—Hairy.

*Color.*—147D.

THE FLOWER

Blooming habit: Recurrent, blooming profusely in the Fall.

Blooms:

*Size.*—Medium. Diameter — About 80 to 100 mm. Depth — About 20 to 30 mm.

*Borne.*—Cyme.

*Shape.*—An almost completely double, composite inflorescence borne on a receptacle surrounded by an involucre of bracts. The shape is generally flat when the bloom first opens and remains flat as the bloom matures.

Petalage:

*Phyllaries.*—About 17 in number.

*Florets.*—Approximately 190 ray florets and many disc florets, the number of which varies.

*Arrangement.*—Imbricated.

*Form.*—Oblanceolate with rounded apex.

*Texture.*—Soft.

*Appearance.*—Satiny.

*Color.*—Ray florets: Top side — 72A-B. Under side — 73B.

Peduncle:

*Length.*—Varies up to about 17 cm.

*Character.*—Strong and upright.

*Color.*—147D.

Discoloration after full bloom: Color fades somewhat as the bloom ages.

Persistence: The florets hang on and dry.

Fragrance: Typical chrysanthemum.

Lasting quality:

*On the plant.*—About three weeks.

*As a cut flower.*—Not recommended.

REPRODUCTIVE ORGANS

Stamens:

*Number.*—Five.

*Arrangement.*—Syngenesious.

*Anthers.*—Of insignificant size and yellow color.

*Filaments.*—Length: Insignificant. Color: Yellow.

*Pollen.*—Color: Yellow.

Pistils:

*Number.*—One for each floret.

*Styles.*—Length: Insignificant. Color: Yellow.

*Stigmas.*—Color: Yellow.

Ovaries: Inferior bicarpellate.

As before mentioned, this new plant is intended for five inch or six inch pot culture and it may be grown the year around with a nine-week response. This plant has its best performance, however, from April through December and is distinguished by its dark pink overall coloring with florets that are slightly quilled to reveal a pink under side, which highlights the dark pink general coloration of the inflorescence.

I claim:

1. A new and distinct dark pink decorative chrysanthemum, substantially as herein shown and described, particularly characterized by the slightly quilled formation of its ray florets which reveal the pale pink coloration of the under side, and its adaptability for five or six inch pot culture the year around under photoperiod control.

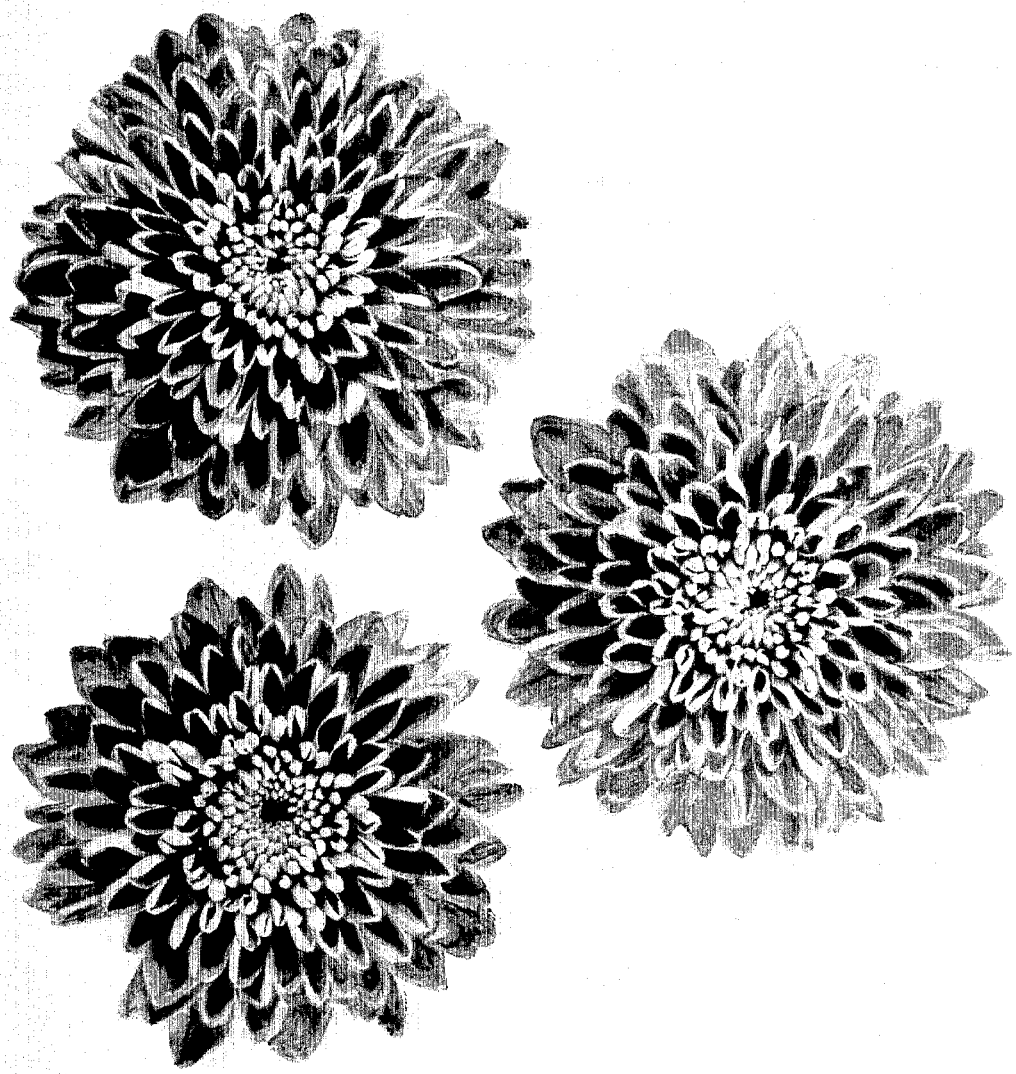

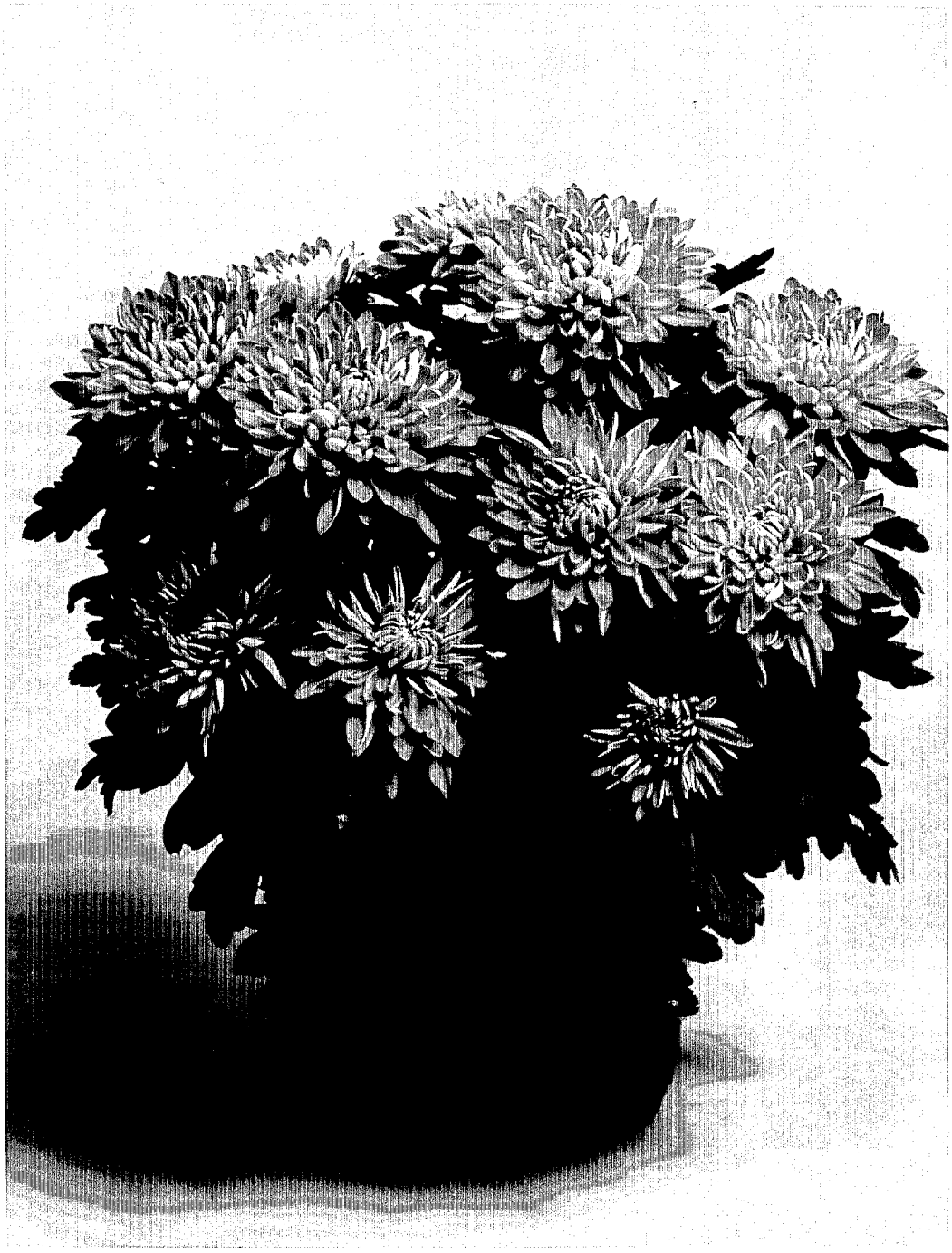

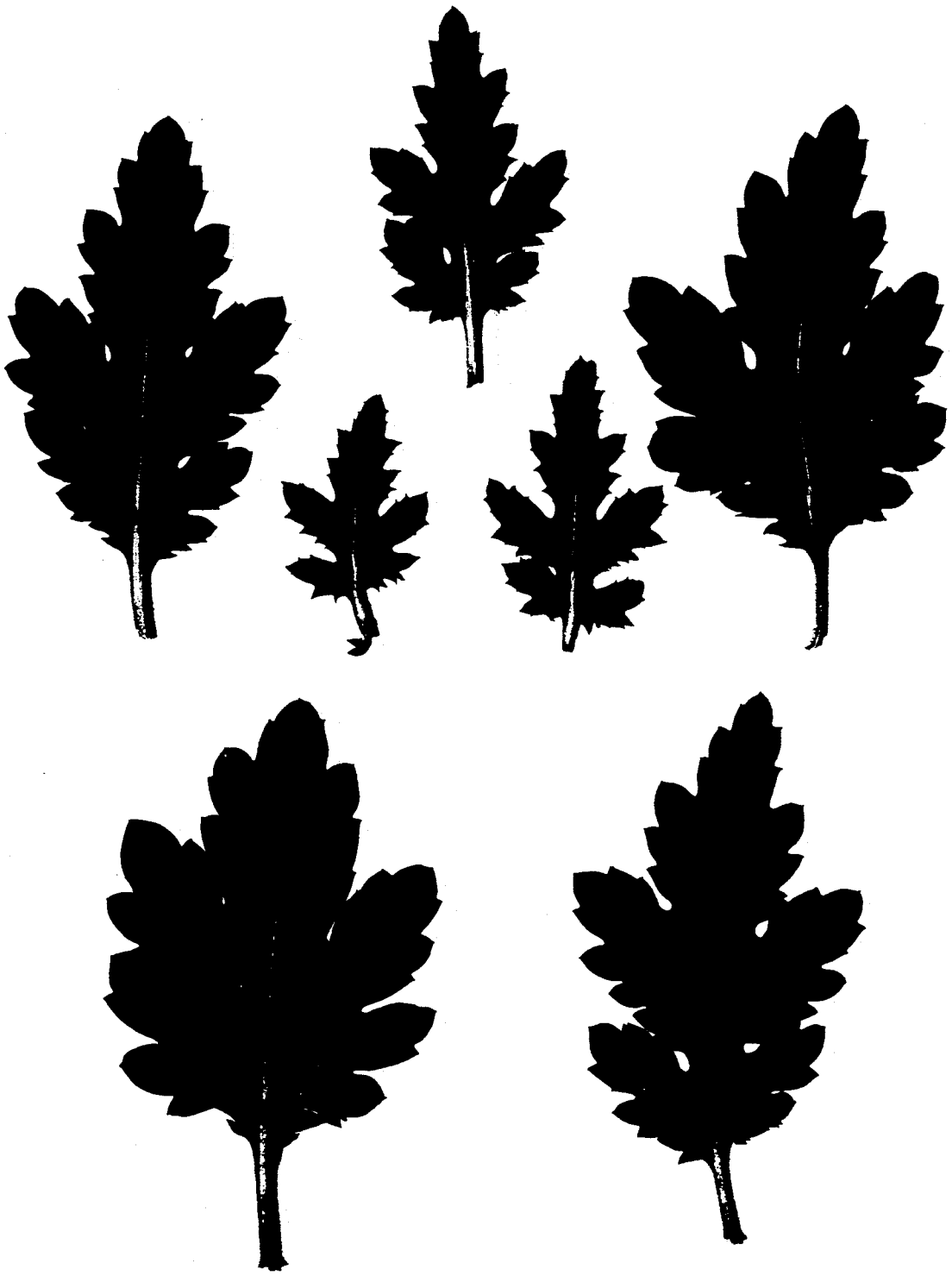

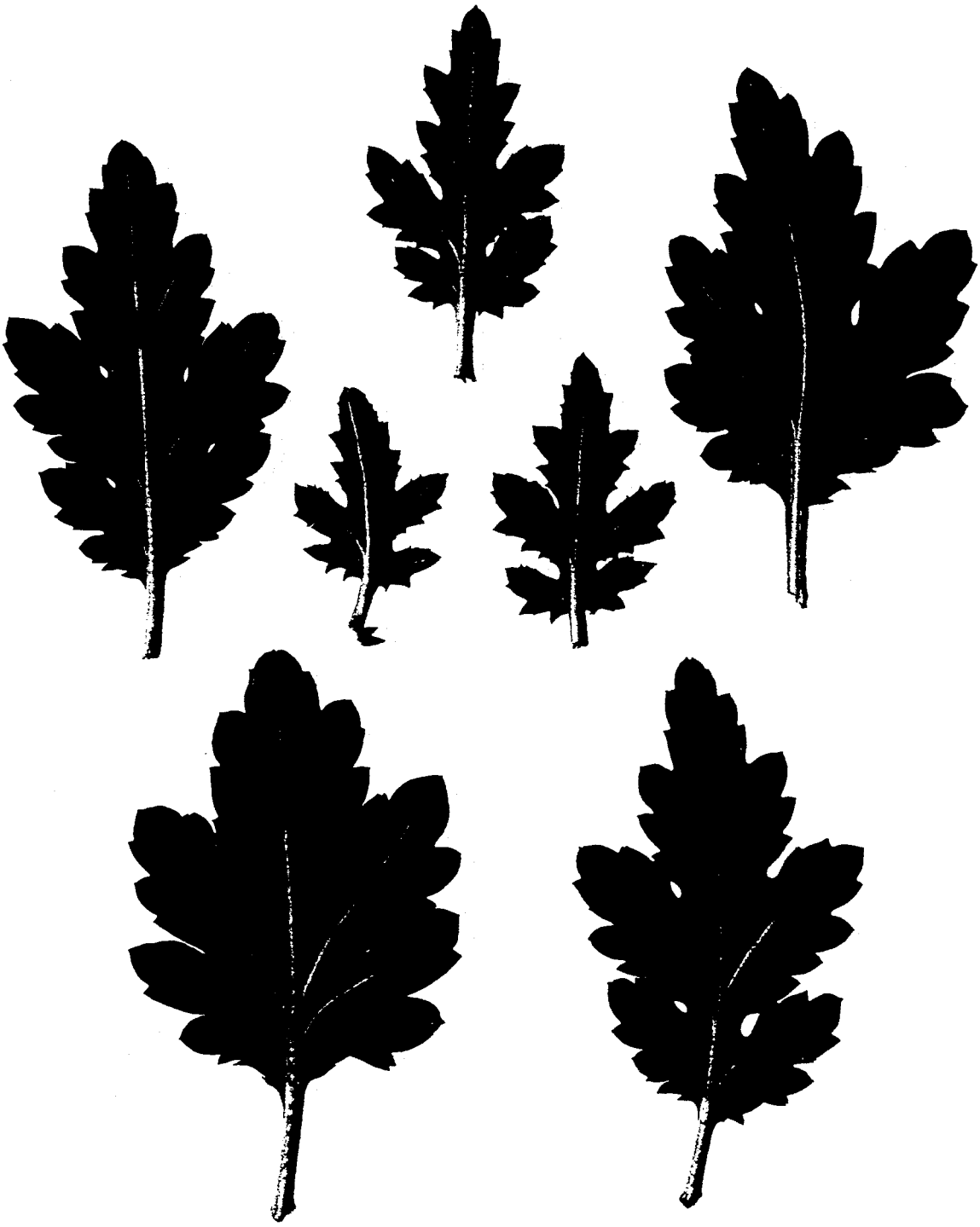

* * * * *